United States Patent
Rogers

(10) Patent No.: US 7,930,191 B1
(45) Date of Patent: Apr. 19, 2011

(54) METHOD AND SYSTEM FOR CORRELATING MEDICAL TREATMENTS WITH SYMPTOMS AND METRICS

(75) Inventor: Lisa Herrup Rogers, Palo Alto, CA (US)

(73) Assignee: Intuit Inc., Mountain View, CA (US)

( * ) Notice: Subject to any disclaimer, the term of this patent is extended or adjusted under 35 U.S.C. 154(b) by 365 days.

(21) Appl. No.: 12/021,708

(22) Filed: Jan. 29, 2008

(51) Int. Cl.
*G06Q 10/00* (2006.01)
*G06Q 50/00* (2006.01)

(52) U.S. Cl. .................................. 705/2; 705/3
(58) Field of Classification Search ............. 705/2–4; 703/11; 600/300
See application file for complete search history.

(56) References Cited

U.S. PATENT DOCUMENTS

| | | | | |
|---|---|---|---|---|
| 6,208,973 B1* | 3/2001 | Boyer et al. | | 705/2 |
| 7,379,885 B1* | 5/2008 | Zakim | | 705/2 |
| 2007/0250352 A1* | 10/2007 | Tawil | | 705/4 |
| 2008/0140371 A1* | 6/2008 | Warner | | 703/11 |
| 2008/0208631 A1* | 8/2008 | Morita et al. | | 705/3 |
| 2009/0024411 A1* | 1/2009 | Albro et al. | | 705/2 |
| 2009/0105550 A1* | 4/2009 | Rothman et al. | | 600/300 |

* cited by examiner

*Primary Examiner* — Luke Gilligan
(74) *Attorney, Agent, or Firm* — Gunnison, McKay & Hodgson, L.L.P.; Philip McKay

(57) ABSTRACT

A method and system for correlating medical treatments with symptoms and metrics includes a process for correlating medical treatments with symptoms and metrics whereby treatment implementation data regarding what medical treatments are prescribed/recommended, and/or employed/implemented by the patient, and when and how the treatments are implemented over a given time frame, is obtained. Patient's specific treatment experience data is also collected that represents the patient's specific treatment experience with, and/or specific results from, the medical treatment over the same time frame. The patient is then provided with processed data correlating the patient's specific treatment experience data with the patient's medical treatment implementation data.

20 Claims, 5 Drawing Sheets

METHOD AND SYSTEM FOR CORRELATING MEDICAL TREATMENTS WITH SYMPTOMS AND METRICS

BACKGROUND

For many prescribed medical treatments, such as, but not limited to: medication; physical therapy; dietary changes; activity level changes; other lifestyle changes; and/or surgical procedures; it is important that the patient perceive a benefit and/or some level of progress as result of the prescribed treatment. Often this perception of benefit/progress is not just important for general patient morale, but the perception itself can often expedite the healing process and/or keep the patient motivated to continue the medical treatment program.

This need to see the benefits/progress associated with a medical treatment is even more pronounced in the modern information age when many people are obsessed with seeing a direct cause-and-effect link with their actions, tracking results, and receiving almost continuous feedback. Despite their desire for information and feedback, currently, most patients undergoing medical treatment have, at best, only a vague sense of whether a prescribed medical treatment is having the desired effect, and these patients typically do not have any sense of how their results measure up to expected and/or average results.

Some patients can, and do, track the effect of a given treatment using any one of several mechanisms ranging from handwritten diary-type records to electronic spread sheets. However, currently, even these "tracker" patients still typically lack the capability and/or data for tracking their individual results against expected or average results; nor do these patients typically have the means or mechanisms for displaying any data they may obtain in any meaningful/useful way.

In addition, many prescribed treatments, particularly medications, have known side-effects and/or predictable stage's of progress/results. In many cases, these side effects are harmless and pass with time. However, it is also often the case that the persistence of these side effects can be an indication of more serious problems and/or reactions to the treatment. Here again, many patients would like, and would benefit from, a capability to track their symptoms/side effects against expected symptoms/side effects and/or the average person's experience. However, currently, patients typically have neither the capability, nor the data, to perform this analysis beyond, at best, some generalized printed materials provided with their treatment and, once again, these patients typically lack the means or mechanisms for displaying any data they may obtain in any meaningful/useful and/or correlated way.

In some cases, patients can, and do, obtain information regarding various medical treatments in general from any one of several secondary data sources such as the Internet. However, the reliability of the information so obtained is often questionable, the information is often inconsistent and/or contradictory from website-to-website, and the information is almost never specific to a given patient. Consequently, even those patients who do track their results/progress, and do seek out more information, often lack confidence in the information itself and are still typically left without any means for comparing and/or displaying results in a meaningful way even if the information obtained were reliable and/or correct.

Many medical treatments require the patient to take proactive steps, and, in many cases, take actions that require self-discipline and/or an investment of time, energy, and money. In addition, many healthcare service providers need to see, or at least would benefit from seeing, results in order to determine the efficacy of a given treatment. Consequently, the current inability to track results in a simple and meaningful way is a very real problem because it can be difficult for the patient to see that their investment/sacrifice is worthwhile. This, in turn, contributes to one of the largest problems facing the healthcare industry today, the problem of patient non-compliance with recommended medical treatments. Each year, patient non-compliance results in avoidable worsening of the patients' condition, avoidable emergency/corrective care costs, and, in some cases, permanent injury to the patients and/or death.

SUMMARY

In accordance with one embodiment, a method and system for correlating medical treatments with symptoms and metrics includes a process for correlating medical treatments with symptoms and metrics whereby, in one embodiment, treatment implementation data regarding what medical treatments are prescribed/recommended, and/or employed/implemented by the patient, over a given time frame is obtained. In one embodiment, patient's specific treatment experience data is also collected that represents the patient's specific treatment experience with, and/or specific results from, the medical treatment over the same time frame. In one embodiment, the patient is then provided with processed data correlating the patient's specific treatment experience data with the patient's medical treatment implementation data. In one embodiment, the patient is also provided the capability to share the processed data with the patient's healthcare service providers, or any designated third party such as a research group.

In one embodiment, baseline medical treatment data associated with a given medical treatment and/or procedure is also obtained. In one embodiment, the baseline medical treatment data includes the expected patient experience and/or results from the medical treatment, and/or an expected time frame for those results, based on the typical patient experience, or the average patient results, and/or other research data. In this embodiment, the patient's specific treatment experience data is compared with the baseline medical treatment data and then this information is provided to the patient. In this way, the patient can view their specific experience with, and/or results from, the medical treatment within the context of the expected and/or average progress/results of the medical treatment.

In one embodiment, the patient's medical treatment implementation data includes, but is not limited to: specific medication and/or medication regimens prescribed to the patient, whether the medications are utilized by the patient, when the medications are utilized by the patient, and/or how the medications are utilized by the patient; specific physical therapy prescribed and implemented, when the therapy is implemented, and/or how the therapy is implemented; dietary changes, along with when and how they are implemented; activity level changes, along with when and how they are implemented; lifestyle changes, along with when and how they are implemented; and/or surgical procedures, along with when and how they are implemented; and/or any other data pertaining to prescribed/recommended medical treatments and the implementation of those prescribed/recommended medical treatments as desired and/or considered necessary by the patient and/or any other party. In one embodiment, the patient's medical treatment implementation data is obtained from various sources, including, but not limited to: healthcare service providers; health insurance providers; health care product providers; the patient; and/or any other party or organization. In one embodiment, the patient's medical treatment implementation data is obtained electronically and/or automatically for the patient. In one embodiment, the patient provides the patient's medical treatment implementation data through manual data entry using a user interface device.

In one embodiment, the patient's specific treatment experience data includes, but is not limited to: specific measurable clinical results and/or metrics from lab results and/or other medical treatment file sources for the patient; specific and general physical and/or mental experiences perceived by the patient; side-effects perceived by the patient; and/or any other data pertaining to the patient's experience as evidenced by either tangible data and/or by patient perception. In one embodiment, the patient's specific treatment experience data is obtained from various sources, including, but not limited to: healthcare service providers; health insurance providers; health care product providers; the patient; and/or any other party or organization. In one embodiment, the patient's specific treatment experience data is obtained electronically and/or automatically for the patient. In one embodiment, the patient provides the patient's specific treatment experience data through manual data entry using a user interface device.

In one embodiment, the baseline medical treatment data includes, but is not limited to: data regarding the expected and/or average results from the medical treatment and how those results are expected to manifest themselves, in terms of both time and the symptom changes; data regarding any side effects associated with the medical treatment, and how those symptom are expected to manifest themselves in terms of both the symptom itself and time; and any other data regarding expected/average results associated with the prescribed medical treatment. In one embodiment, the baseline medical treatment data is obtained from various sources, including, but not limited to: medication manufacturers and/or providers; clinical studies; government agencies; public and private watchdog groups; healthcare service providers; health insurance providers; health care product providers; the patient; and/or any other party or organization. In one embodiment, the baseline medical treatment data is obtained electronically and/or automatically for the patient. In one embodiment, the baseline medical treatment data is obtained through manual data entry using a user interface device.

In one embodiment, the processed data correlating the patient's specific treatment experience data with the patient's medical treatment implementation data is provided to the patient in the form of a visual display such as, but not limited to: a graphical display of results over time; a charting of results over time; a video representation; or any other primarily visual display. In other embodiments, the processed data correlating the patient's specific treatment experience data with the patient's medical treatment implementation data is provided to the patient in the form of an audio presentation, in a table of data, or in text format. In one embodiment, the processed data correlating the patient's specific treatment experience data with the patient's medical treatment implementation data is provided to the patient in any format capable of conveying comparative/correlated data to a patient, whether known at the time of filing or as developed thereafter.

In one embodiment, the processed data representing the patient's specific treatment experience data compared with the baseline medical treatment data is provided to the patient in the form of a visual display such as, but not limited to: a graphical display of results over time; a charting of results over time; a display of the patient's specific treatment experience data compared with non-temporal averages, benchmarks, and/or typical results or data; a video representation; or any other primarily visual display. In other embodiments, the processed data representing the patient's specific treatment experience data compared with the baseline medical treatment data is provided to the patient in the form of an audio presentation, as a table of data, or in text format. In one embodiment, the processed data representing the patient's specific treatment experience data compared with the baseline medical treatment data is provided to the patient in any format capable of conveying comparative/correlated data to a patient, whether known at the time of filing or as developed thereafter.

In one embodiment, the patient's specific treatment experience data is correlated with the patient's medical treatment implementation data, or any other patient data desired, using mathematical and/or statistical analysis, such as regression analysis, and the correlation, along with an analysis of how strongly the data is correlated, is provided to the patient, healthcare service providers, and/or any other designated parties.

In some embodiments, the patient is provided with proactive notices, alerts, and/or reminders, based on the processed data and representing, among other things, recommended/required healthcare provider appointments, tests, and/or any changes in status. In one embodiment, the patient is provided with commentary regarding the processed data including, but not limited to, advice and counseling. In one embodiment, the proactive notices, alerts, reminders, and/or commentary regarding the processed data are provided to the patient in the form of a visual display. In one embodiment, the proactive notices, alerts, reminders, and/or commentary regarding the processed data are provided to the patient in the form of an audio presentation, and/or as a table of data, and/or in text format. In one embodiment, the proactive notices, alerts, reminders, and/or commentary regarding the processed data are provided to the patient in any format and/or by any mechanism capable of conveying comparative/correlated data to a patient, whether known at the time of filing or as developed thereafter.

Using the method and system for correlating medical treatments with symptoms and metrics disclosed herein, a patient is provided information showing his or her results and/or progress correlated with the implementation of a given medical treatment. In addition, in one embodiment, using the method and system for correlating medical treatments with symptoms and metrics disclosed herein, a patient is provided information showing his or her results and/or progress as compared with expected results and/or progress for a given treatment. Consequently, using the method and system for correlating medical treatments with symptoms and metrics disclosed herein, the patient is provided feedback and comparative information showing the results and/or progress of his or her efforts. In many cases, this feedback further provides the positive reinforcement necessary to keep the patient on the prescribed medical treatment. In addition, many patients may feel empowered and inspired by this information to take a more active role in maintaining their bodies and tracking their general state of health.

As discussed in more detail below, using the below embodiments, with little or no modification and/or user input, there is considerable flexibility, adaptability, and opportunity for customization to meet the specific needs of various users under numerous circumstances.

Figure 1:
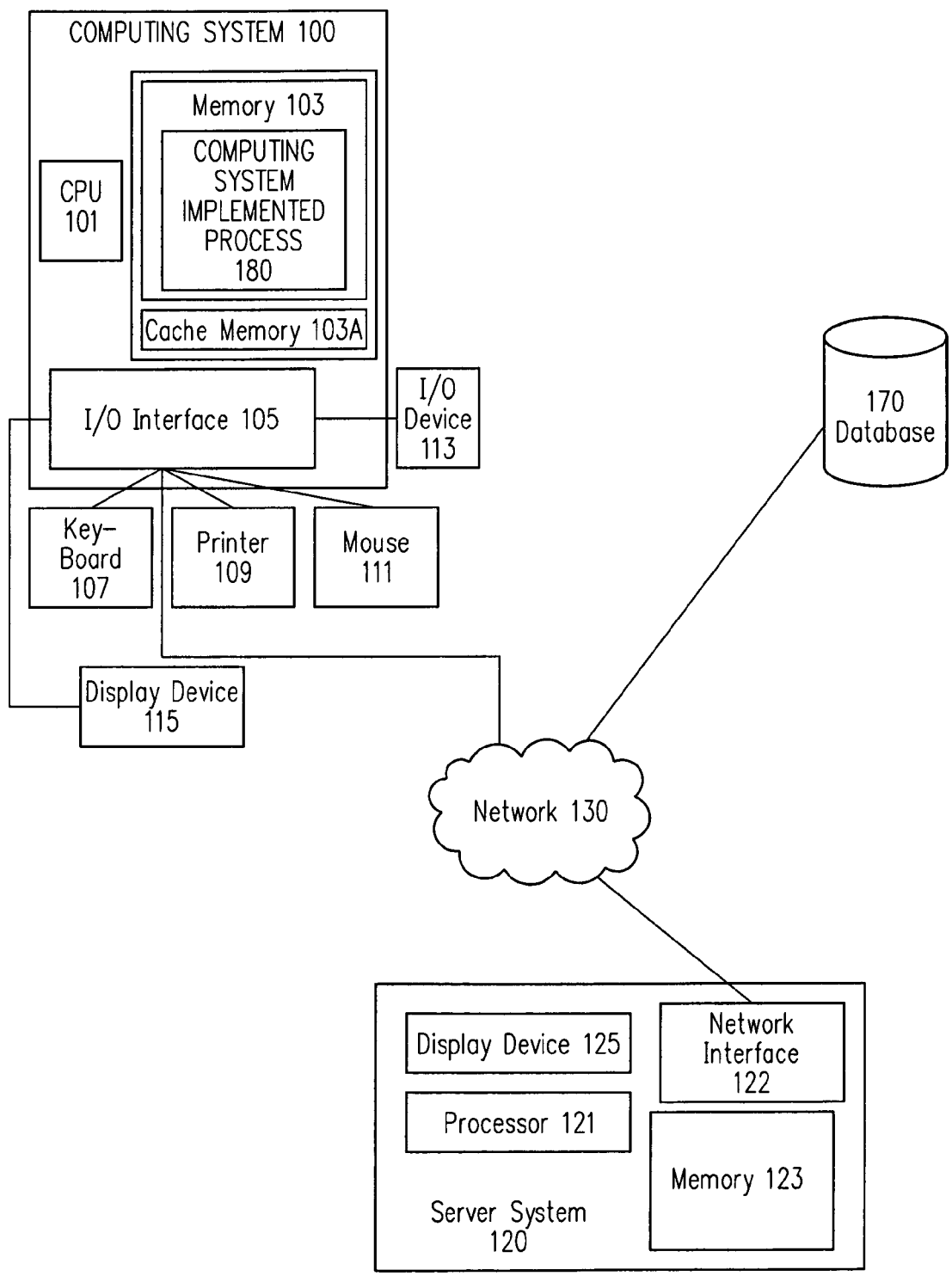
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

In accordance with one embodiment, a method and system for correlating medical treatments with symptoms and metrics includes a process for correlating medical treatments with symptoms and metrics whereby, in one embodiment, treatment implementation data regarding what medical treatments are prescribed/recommended, and/or employed/implemented by the patient, over a given time frame is obtained. In one embodiment, patient's specific treatment experience data is also collected that represents the patient's specific treatment experience with, and/or specific results from, the medical treatment over the same time frame. In one embodiment, the patient is then provided with processed data correlating the patient's specific treatment experience data with the patient's medical treatment implementation data.

In one embodiment, baseline medical treatment data associated with a given medical treatment and/or procedure is also obtained. In one embodiment, the baseline medical treatment data includes the expected patient experience and/or results from the medical treatment, and/or an expected time frame for those results, based on the typical patient experience and/or research data. In this embodiment, the patient's specific treatment experience data is compared with the baseline medical treatment data and then this information is provided to the patient. In this way, the patient can view their specific experience with, and/or results from, the medical treatment within the context of the expected and/or average progress/results of the medical treatment.

In one embodiment, the patient's medical treatment implementation data includes, but is not limited to: specific medication and/or medication regimens prescribed to the patient, whether the medications are utilized by the patient, when the medications are utilized by the patient, and/or how the medications are utilized by the patient; specific physical therapy prescribed and implemented, when the therapy is implemented, and/or how the therapy is implemented; dietary changes, along with when and how they are implemented; activity level changes, along with when and how they are implemented; lifestyle changes, along with when and how they are implemented; and/or surgical procedures, along with when and how they are implemented; and/or any other data pertaining to prescribed/recommended medical treatments and the implementation of those prescribed/recommended medical treatments as desired and/or considered necessary by the patient and/or any other party. In one embodiment, the patient's medical treatment implementation data is obtained from various sources, including, but not limited to: healthcare service providers; health insurance providers; health care product providers; the patient; and/or any other party or organization. In one embodiment, the patient's medical treatment implementation data is obtained electronically and/or automatically for the patient. In one embodiment, the patient provides the patient's medical treatment implementation data through manual data entry using a user interface device.

In one embodiment, the patient's specific treatment experience data includes, but is not limited to: specific measurable clinical results and/or metrics from lab results and/or other medical treatment file sources for the patient; specific and general physical and/or mental experiences perceived by the patient; side-effects perceived by the patient; and/or any other data pertaining to the patient's experience as evidenced by either tangible data and/or by patient perception. In one embodiment, the patient's specific treatment experience data is obtained from various sources, including, but not limited to: healthcare service providers; health insurance providers; health care product providers; the patient; and/or any other professional, medical service provider, party or organization. In one embodiment, the patient's specific treatment experience data is obtained electronically and/or automatically for the patient. In one embodiment, the patient, or other designated party, provides the patient's specific treatment experience data through manual data entry using a user interface device.

In one embodiment, the baseline medical treatment data includes, but is not limited to: data regarding the expected results from the medical treatment and how those results are expected to manifest themselves, in terms of both time and the symptom changes; data regarding any side effects associated with the medical treatment, and how those symptom are expected to manifest themselves in terms of both the symptom itself and time; and any other data regarding expected/average results associated with the prescribed medical treatment. In one embodiment, the baseline medical treatment data is obtained from various sources, including, but not limited to: medication manufacturers and/or providers; clinical studies; government agencies; public and private watchdog groups; healthcare service providers; health insurance providers; health care product providers; the patient; and/or any other party or organization. In one embodiment, the baseline medical treatment data is obtained electronically and/or automatically for the patient. In one embodiment, the baseline medical treatment data is obtained through manual data entry using a user interface device.

In one embodiment, the processed data correlating the patient's specific treatment experience data with the patient's medical treatment implementation data is provided to the patient in the form of a visual display such as, but not limited to: a graphical display of results over time; a charting of results over time; a video representation; or any other primarily visual display. In other embodiments, the processed data correlating the patient's specific treatment experience data with the patient's medical treatment implementation data is provided to the patient in the form of an audio presentation, in a table of data, or in text format. In one embodiment, the processed data correlating the patient's specific treatment experience data with the patient's medical treatment implementation data is provided to the patient in any format capable of conveying comparative/correlated data to a patient, whether known at the time of filing or as developed thereafter.

In one embodiment, the processed data representing the patient's specific treatment experience data compared with the baseline medical treatment data is provided to the patient in the form of a visual display such as, but not limited to: a graphical display of results over time; a charting of results over time; a video representation; or any other primarily visual display. In other embodiments, the processed data representing the patient's specific treatment experience data compared with the baseline medical treatment data is provided to the patient in the form of an audio presentation, as a table of data, or in text format. In one embodiment, the processed data representing the patient's specific treatment experience data compared with the baseline medical treatment data is provided to the patient in any format capable of conveying comparative/correlated data to a patient, whether known at the time of filing or as developed thereafter.

Using the method and system for correlating medical treatments with symptoms and metrics disclosed herein, a patient is provided information showing his or her results and/or progress correlated with the implementation of a given medical treatment. In addition, in one embodiment, using the method and system for correlating medical treatments with symptoms and metrics disclosed herein, a patient is provided information showing his or her results and/or progress as compared with expected results and/or progress for a given treatment. Consequently, using the method and system for correlating medical treatments with symptoms and metrics disclosed herein, the patient is provided feedback and comparative information showing the results and/or progress of his or her efforts. In many cases, this feedback further provides the positive reinforcement necessary to keep the patient on the prescribed medical treatment. In addition, many patients may feel empowered and inspired by this information to take a more active role in maintaining their bodies and tracking their general state of health.

As discussed in more detail below, using the below embodiments, with little or no modification and/or user input, there is considerable flexibility, adaptability, and opportunity for customization to meet the specific needs of various users under numerous circumstances.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian® OS, Windows® Mobile, or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, or other computing system capable of processing computer readable data, whether known at the time of filing or as developed later. Computing systems also include those in which one or more computing resources (hardware or software) are located remotely and accessed via network, such as a Local Area Network (LAN), Wide Area Network (WAN), a public network, such as the Internet, a private network, a combination of network types, a computing system bus, or other electronic medium in which data may be exchanged between one computing system and one or more other computing system(s), whether known at the time of filing or as developed later. Embodiments may be included as add-on software for existing software programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

Hardware System Architecture

FIG. 1 is a block diagram of exemplary hardware architecture for implementing one embodiment of a process for correlating medical treatments with symptoms and metrics, such as exemplary processes for correlating medical treatments with symptoms and metrics 200, discussed below, that includes: a computing system 100; a server system 120; and a database 170, all operatively connected by a network 130.

As seen in FIG. 1, computing system 100 typically includes a processor 101, an input/output (I/O) interface 105, and a memory system 103, including cache memory 103A. In one embodiment, computing system 100 includes all or part of one or more computing system implemented processes 180 such as, but not limited to, a computing system implemented healthcare management system that is a used by, is a parent system for, is accessed by, and/or is otherwise associated with, a process for correlating medical treatments with symptoms and metrics, such as exemplary processes for correlating medical treatments with symptoms and metrics 200.

Computing system 100 may further include standard user interface devices such as a keyboard 107, a mouse 111, a printer 109, and a display device 115, as well as, one or more standard input/output (I/O) devices 113, such as a compact disk (CD) or DVD drive, floppy disk drive, or other digital or waveform port, or other device capable of inputting data to, and outputting data from, computing system 100, whether known at the time of filing or as later developed. As discussed in more detail below, in one embodiment, a process for correlating medical treatments with symptoms and metrics, and/or one or more computing system implemented processes, can be loaded, in whole, or in part, into computing system 100 via I/O device 113, such as from a CD, DVD or floppy disk containing all, or part, of a process for correlating medical treatments with symptoms and metrics and/or a computing system implemented process.

Also shown in FIG. 1 is database 170. In one embodiment, database 170 is a designated server system or computing system, or a designated portion of a server system or computing system, such as computing systems 100 and 120. In one embodiment, database 170 is a dedicated mass storage device implemented in software, hardware, or a combination of hardware and software. In one embodiment, database 170 is a web-based function and/or website. As discussed in more detail below, in one embodiment, a process for correlating medical treatments with symptoms and metrics, and/or one or more computing system implemented processes, is/are stored in whole, or in part, in database 170.

In one embodiment, computing system 100 and database 170, are coupled to a server system 120 by network 130. Server system 120 typically includes a server system display device 125, a server system processor 121, a server system memory 123, and a server system network interface 122. As discussed in more detail below, in one embodiment, a process for correlating medical treatments with symptoms and metrics, and/or one or more computing system implemented processes, is/are stored in whole, or in part, in server system 120.

Network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether known at the time of filing or as later developed. In various embodiments, server system network interface 122 and I/O interface 105 include analog modems, digital modems, a network interface card, a broadband connection, or any other means for communicably coupling computing system 100, database 170, and server system 120, via network 130, whether known at the time of filing or as later developed.

Those of skill in the art will readily recognize that the components shown in FIG. 1, such as computing system 100, database 170, server system 120, and their respective components, are shown for illustrative purposes only and that architectures with more or fewer components can implement, and benefit from, a process for correlating medical treatments with symptoms and metrics, such as exemplary process for correlating medical treatments with symptoms and metrics 200 discussed below. Moreover, one or more components of computing system 100, database 170, and server system 120 may be located remotely from their respective system and accessed via a network, as discussed herein. In addition, the particular type of, and configuration of, computing systems 100, database 170, and server system 120 are not relevant.

As discussed in more detail below, in one embodiment, a process for correlating medical treatments with symptoms and metrics, and/or one or more computing system implemented processes, is/are stored in whole, or in part, in memory system 103 and/or cache memory 103A, of computing system 100, and/or in server memory system 123 of server system 120 and/or in database 170, and executed on computing system 100. As used herein, a memory refers to a volatile memory, a non-volatile memory, or any combination of the two.

Although a process for correlating medical treatments with symptoms and metrics, and/or one or more computing system implemented processes, can sometimes be referred to herein, alternatively, as a process, an application, a module, a program, a component of a software system, a component of a software package, a component of a parent system, or a feature of a parent system, this terminology is illustrative only. In some embodiments, a process for correlating medical treatments with symptoms and metrics, and/or one or more computing system implemented processes, is/are capable of being called from an application or the operating system. In one embodiment, an application or program is generally defined to be any executable code. Moreover, those of skill in the art will understand that when it is said that an application or an operation takes some action, the action is the result of executing one or more instructions by a processor, such as processor 101 or server system processor 121. In one embodiment, execution of a process for correlating medical treatments with symptoms and metrics, and/or one or more computing system implemented processes, by processor 101 or server system processor 121, results in the operations of an agent computer process (not shown) and/or a rule computer process (not shown).

In one embodiment, a process for correlating medical treatments with symptoms and metrics, and/or one or more computing system implemented processes, is/are a computer application or process implemented and/or run and/or stored, in full, or in part, in, or on, a computer program product. Herein, a computer program product comprises a medium configured to store and/or transport computer readable code, whether known at the time of filing or as later developed. Some examples of computer program products are CD-ROM discs, DVDs, ROM cards, floppy discs, magnetic tapes, computer hard drives, servers on a network, such as server system 120 of FIG. 1, and signals transmitted over a network, such as network 130 of FIG. 1, or other media or process capable of delivering computer readable data representing computer readable code, whether known at the time of filing or as later developed. This medium may belong to a computing system, such as computing system 100 of FIG. 1, described above. However, the medium also may be removed from the computing system.

For example, all, or part, of a process for correlating medical treatments with symptoms and metrics, and/or one or more computing system implemented processes, may be stored in a memory that is physically located in a location, such as server system memory 123, or database 170, of FIG. 1, different from a computing system, such as computing system 100 of FIG. 1, utilizing a process for correlating medical treatments with symptoms and metrics, and/or one or more computing system implemented processes. In one embodiment, all, or part, of a process for correlating medical treatments with symptoms and metrics, and/or one or more computing system implemented processes, may be stored in a memory that is physically located, separate from the computing system's processor(s), such as processor 101 of FIG. 1, and the computing system processor(s) can be coupled to the memory in a client-server system, such as server system 120 of FIG. 1, or, alternatively, via connection to another computer, such as computing system 100 of FIG. 1, via modems and analog lines, digital interfaces and a digital carrier line, or wireless or cellular connections.

In one embodiment, the computing systems and/or server system, such as computing system 100 and/or server system 120 of FIG. 1, running and/or utilizing and/or storing all, or part, of a process for correlating medical treatments with symptoms and metrics, and/or one or more computing system implemented processes, is a portable computer, a workstation, a two-way pager, a cellular telephone, a smart phone, a digital wireless telephone, a personal digital assistant, a server computer, an Internet appliance, or any other device that includes components that can execute all, or part, of a process for correlating medical treatments with symptoms and metrics, and/or one or more computing system implemented processes, in accordance with at least one of the embodiments as described herein. Similarly, in another embodiment, a process for correlating medical treatments with symptoms and metrics, and/or one or more computing system implemented processes, is/are implemented on and/or run and/or stored on a computing system and/or server system that is comprised of multiple different computers, wireless devices, cellular telephones, digital telephones, two-way pagers, personal digital assistants, server computers, or any desired combination of these devices, that are interconnected to perform the processes as described herein.

Process

Herein, the terms "patient", "user", "patient/user" and "user/patient", are used interchangeably to denote: any person or persons, such as an individual or family representative, a healthcare plan administrator, a healthcare service provider, or any institution, such as a healthcare service provider or health insurance provider; any agent of a person or persons; any agent of an institution; or any other individual or group utilizing, implementing, participating in, and/or providing, and/or facilitating, and/or administering, a medical treatment plan/program and/or a healthcare plan/program and/or a method, system or process for correlating medical treatments with symptoms and metrics as disclosed herein.

Herein, the term "medical treatment" includes, but is not limited to: one or more medications and/or medication regimens; physical therapy; dietary changes; activity level changes; other lifestyle changes; and/or surgical procedures; and/or any prescribed and/or suggested regime, medication, treatment, activity, avoided activity, and/or program designed to improve, maintain, and/or slow the degradation of, a patients health in light of specific, non-specific, and/or general condition and/or state of health.

In accordance with one embodiment, a method and system for correlating medical treatments with symptoms and metrics includes a process for correlating medical treatments with symptoms and metrics whereby, in one embodiment, treatment implementation data regarding what medical treatments are prescribed/recommended, and/or employed/implemented by the patient, and/or a designated party for, or on behalf of, the patient, and when and how the treatments are implemented, over a given time frame, is obtained. In one embodiment, a patient's specific treatment experience data is also collected that represents the patient's specific treatment experience with, and/or specific results from, the medical treatment over the same time frame. In one embodiment, the patient is then provided with processed data correlating the patient's specific treatment experience data with the patient's medical treatment implementation data.

Figure 2:
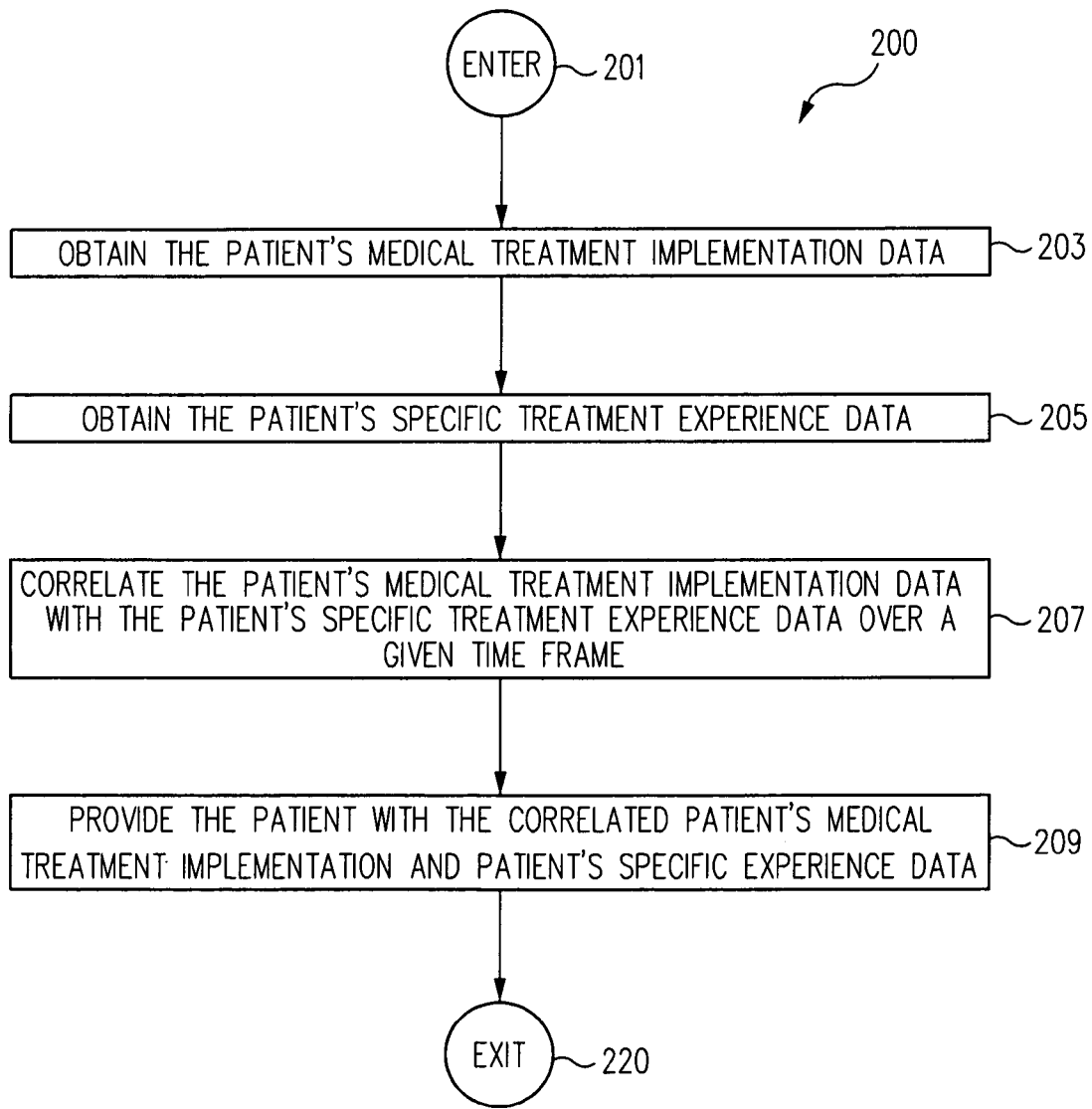
FIG. 2 is a flow chart depicting a process for correlating medical treatments with symptoms and metrics in accordance with one embodiment.

FIG. 2 is a flow chart depicting a process for correlating medical treatments with symptoms and metrics 200 in accordance with one embodiment. Process for correlating medical treatments with symptoms and metrics 200 begins at ENTER OPERATION 201 of FIG. 2 and process flow proceeds to OBTAIN THE PATIENT'S MEDICAL TREATMENT IMPLEMENTATION DATA OPERATION 203.

In one embodiment, at OBTAIN THE PATIENT'S MEDICAL TREATMENT IMPLEMENTATION DATA OPERATION 203 data regarding the patient's prescribed/recommended medical treatment, and the implementation/use of any treatments, is obtained and/or updated.

As noted above, herein, the term "medical treatment" includes, but is not limited to: one or more medications and/or medication regimens; physical therapy; dietary changes; activity level changes; other lifestyle changes; and/or surgical procedures; and/or any prescribed and/or suggested regime, medication, treatment, activity, avoided activity, and/or program designed to improve, maintain, and/or slow the degradation of, a patients health in light of specific, non-specific, and/or general condition and/or state of health.

In one embodiment, the patient's medical treatment implementation data obtained at OBTAIN THE PATIENT'S MEDICAL TREATMENT IMPLEMENTATION DATA OPERATION 203, includes, but is not limited to, one or more of the following: specific medication and/or medication regimens prescribed to the patient, the dosage/repetition prescribed, whether the medication is utilized by the patient, and/or when the medication is taken; specific physical therapy prescribed and implemented, how often the therapy is repeated, when the therapy is performed, and how it is implemented; dietary changes including foods and/or beverages consumed, or not consumed, when food and/or beverage is ingested, and how much is consumed; activity level changes including what activity is performed, how often and when; lifestyle changes, along with when and how they are implemented; and/or surgical procedures, along with when and how they are implemented; and/or any other data pertaining to prescribed/recommended medical treatments, and the implementation of those prescribed/recommended medical treatments, as desired and/or considered necessary by the patient and/or any other party.

In one embodiment, the patient's medical treatment implementation data is obtained from various sources, including, but not limited to: healthcare service providers; health insurance providers; health care product providers; the patient; and/or any other party or organization.

As an example, in one embodiment, the patient's medical treatment implementation data is obtained at OBTAIN THE PATIENT'S MEDICAL TREATMENT IMPLEMENTATION DATA OPERATION 203 directly from the patient. In one embodiment, the data is provided to process for correlating medical treatments with symptoms and metrics 200 at OBTAIN THE PATIENT'S MEDICAL TREATMENT IMPLEMENTATION DATA OPERATION 203 by entering the data into a user interface displayed on a computing system, such as computing system 100 described above. In other embodiments, the data is obtained at OBTAIN THE PATIENT'S MEDICAL TREATMENT IMPLEMENTATION DATA OPERATION 203 by any means for obtaining, collecting, accessing, entering, transferring, relaying and/or providing data in any form, to a process, such as process for correlating medical treatments with symptoms and metrics 200, whether known at the time of filing or as developed thereafter.

In one embodiment, process for correlating medical treatments with symptoms and metrics 200 is part of a parent personal health management, personal financial, business financial, accounting, or tax preparation software system, program, package, website, or application, such as computing system implemented process 180 of FIG. 1, that implements, includes, is accessed by, and/or is otherwise associated with process for correlating medical treatments with symptoms and metrics 200, typically as one of multiple features. In these embodiments, the data representing the patient's medical treatment implementation may be obtained directly from, or through, the parent process.

In one embodiment, the patient's medical treatment implementation data is obtained at OBTAIN THE PATIENT'S MEDICAL TREATMENT IMPLEMENTATION DATA OPERATION 203 from invoices/patient bills, records of purchases, and/or insurance claim data provided to process for correlating medical treatments with symptoms and metrics 200 by health insurance providers and/or health care providers such as hospitals and/or doctors and/or other medical service personnel.

As noted above, in one embodiment, process for correlating medical treatments with symptoms and metrics 200 is part of a parent computing system implemented process that implements, includes, is accessed by, and/or is otherwise associated with process for correlating medical treatments with symptoms and metrics 200, as one of multiple features. Some of these parent systems provide the capability to obtain, receive, and/or process electronic copies of the invoices/claims, often in their specific formats, and then store the data for use by process for correlating medical treatments with symptoms and metrics 200 in one of numerous locations by one of numerous methods known to those of skill in the art.

In one embodiment, the patient's medical treatment implementation data is obtained at OBTAIN THE PATIENT'S MEDICAL TREATMENT IMPLEMENTATION DATA OPERATION 203 from Explanation of Benefits (EOB) data provided to process for correlating medical treatments with symptoms and metrics 200 by a health insurance provider and/or the user of process for correlating medical treatments with symptoms and metrics 200.

According to one embodiment, the health insurance providers transfer electronic copies of the EOBs, often in specific formats, to the provider of process for correlating medical treatments with symptoms and metrics 200. According to one embodiment, the health insurance providers transfer electronic copies of the EOBs, often in specific formats, to a parent computing system implemented process that is a parent system for process for correlating medical treatments with symptoms and metrics 200. Some of these parent computing system implemented processes provide the capability to obtain, receive, and/or process electronic copies of the EOBs and then store the data for use by process for correlating medical treatments with symptoms and metrics 200 in one of numerous locations by one of numerous methods known to those of skill in the art.

In some embodiments, the patient's medical treatment implementation data is obtained at OBTAIN THE PATIENT'S MEDICAL TREATMENT IMPLEMENTATION DATA OPERATION 203 from any combination of the above sources and/or from any other source of data, whether known at the time of filing or as developed thereafter.

In one embodiment, the data representing the patient's medical treatment implementation is stored, in whole, or in part, in a database maintained by, accessible by, owned by, or otherwise related to, a provider of process for correlating medical treatments with symptoms and metrics 200 by any one of the numerous mechanisms known to those of skill in the art. For instance, in one embodiment, the data, in whole, or in part, is stored in a memory system, such as memory system 103, or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system and/or on a public network such as the Internet.

Returning to FIG. 2, in some embodiments, the data stored as described above is maintained, in whole, or in part, by: the provider of process for correlating medical treatments with symptoms and metrics 200; a computing system implemented process that is a parent for process for correlating medical treatments with symptoms and metrics 200; the patient; a health insurance provider; a healthcare service provider; a third party data storage institution; any third party service or institution; or any other parties. In these embodiments, access to the data is then granted to process for correlating medical treatments with symptoms and metrics 200 at OBTAIN THE PATIENT'S MEDICAL TREATMENT IMPLEMENTATION DATA OPERATION 203 by providing access to the data and/or providing the data on a computer program product.

In other embodiments, the data representing the patient's medical treatment implementation is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the data representing the patient's medical treatment implementation is obtained/accessed/collected through e-mail or through text messaging. In other embodiments, the data representing the patient's medical treatment implementation is provided to process for correlating medical treatments with symptoms and metrics 200 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once data regarding the patient's prescribed/recommended medical treatment, and the implementation/use of those treatments, is obtained and/or updated at OBTAIN THE PATIENT'S MEDICAL TREATMENT IMPLEMENTATION DATA OPERATION 203, process flow proceeds to OBTAIN THE PATIENT'S SPECIFIC TREATMENT EXPERIENCE DATA OPERATION 205.

In one embodiment, at OBTAIN THE PATIENT'S SPECIFIC TREATMENT EXPERIENCE DATA OPERATION 205, data regarding the patient's specific treatment experience with the prescribed/recommended medical treatment is obtained. In one embodiment, the patient's specific treatment experience data includes, but is not limited to: specific measurable clinical results and/or metrics from lab results, charts, medical records, and/or other medical treatment data sources for the patient; specific and general physical and/or mental experiences perceived by the patient, including experiences not subject to measurement and/or empirical analysis; side-effects perceived by the patient, the symptoms of the side-effects, the severity of the symptoms, and the duration of the side-effect symptoms; any patient discomfort and/or relief associated with the medical treatment and/or how the treatment makes the patient "feel"; and/or any other data pertaining to the patient's experience as evidenced by either tangible data and/or by patient perception and/or intuition.

In one embodiment, the patient's specific treatment experience data is obtained from various sources, including, but not limited to: healthcare service providers; health insurance providers; health care product providers; the patient; various medical and/or monitoring devices, and/or any other machine, party, or organization.

As an example, in one embodiment, the patient's specific treatment experience data is obtained at OBTAIN THE PATIENT'S SPECIFIC TREATMENT EXPERIENCE DATA OPERATION 205 directly from the patient. In one embodiment, the data is provided to process for correlating medical treatments with symptoms and metrics 200 at OBTAIN THE PATIENT'S SPECIFIC TREATMENT EXPERIENCE DATA OPERATION 205 by entering the data into a user interface displayed on a computing system, such as computing system 100 described above. In other embodiments, the data is obtained at OBTAIN THE PATIENT'S SPECIFIC TREATMENT EXPERIENCE DATA OPERATION 205 by any means for obtaining, collecting, accessing, entering, transferring, relaying and/or providing data in any form, to a process, such as process for correlating medical treatments with symptoms and metrics 200, whether known at the time of filing or as developed thereafter.

For example, as noted above, in one embodiment, process for correlating medical treatments with symptoms and metrics 200 is part of a parent personal health management, personal financial, business financial, accounting, or tax preparation software system, program, package or application, such as computing system implemented process 180 of FIG. 1, that implements, includes, is accessed by, and/or is otherwise associated with process for correlating medical treatments with symptoms and metrics 200, typically as one of multiple features. In these embodiments, the data representing the patient's specific treatment experience may be obtained directly from, or through, the parent process.

In one embodiment, the patient's specific treatment experience data is obtained at OBTAIN THE PATIENT'S SPECIFIC TREATMENT EXPERIENCE DATA OPERATION 205 from invoices/patient bills and/or claim data provided to process for correlating medical treatments with symptoms and metrics 200 by health care providers such as hospitals and/or doctors and/or other medical service personnel.

As noted above, in one embodiment, process for correlating medical treatments with symptoms and metrics 200 is part of a parent computing system implemented process. Some of these parent systems provide the capability to obtain, receive, and/or process electronic copies of the invoices/claims, often in their specific formats, and then store the data for use by process for correlating medical treatments with symptoms and metrics 200 in one of numerous locations by one of numerous methods known to those of skill in the art.

In one embodiment, the patient's specific treatment experience data is obtained at OBTAIN THE PATIENT'S SPECIFIC TREATMENT EXPERIENCE DATA OPERATION 205 from data provided to process for correlating medical treatments with symptoms and metrics 200 by a health insurance provider and/or the user of process for correlating medical treatments with symptoms and metrics 200.

In some embodiments, the patient's specific treatment experience data is obtained at OBTAIN THE PATIENT'S SPECIFIC TREATMENT EXPERIENCE DATA OPERATION 205 from any combination of the above sources and/or from any other source of data, whether known at the time of filing or as developed thereafter.

In one embodiment, the data representing the patient's specific treatment experience is stored, in whole, or in part, in a database maintained by, accessible by, owned by, or otherwise related to, a provider of process for correlating medical treatments with symptoms and metrics 200 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, the data stored as described above is maintained, in whole, or in part, by: the provider of process for correlating medical treatments with symptoms and metrics 200; a computing system implemented process that is a parent process for process for correlating medical treatments with symptoms and metrics 200; the patient; a health insurance provider; a healthcare service provider; a third party data storage institution; any third party service or institution; or any other parties. In these embodiments, access to the data is then granted to process for correlating medical treatments with symptoms and metrics 200 at OBTAIN THE PATIENT'S SPECIFIC TREATMENT EXPERIENCE DATA OPERATION 205 by providing access to the data and/or providing the data on a computer program product.

In other embodiments, the data representing the patient's specific treatment experience is provided through a network of computing systems and/or server systems that is comprised of multiple different computers, wireless, devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the data representing the patient's specific treatment experience is obtained/accessed/collected through e-mail or through text messaging. In other embodiments, the data representing the patient's specific treatment experience is provided to process for correlating medical treatments with symptoms and metrics 200 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once data regarding the patient's specific treatment experience with the prescribed/recommended medical treatment is obtained at OBTAIN THE PATIENT'S SPECIFIC TREATMENT EXPERIENCE DATA OPERATION 205, process flow proceeds to CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207.

In one embodiment, at CORRELATE THE PATIENT'S MEDICAL TREATMENT IMPLEMENTATION DATA WITH THE PATIENT'S SPECIFIC TREATMENT EXPE- RIENCE DATA OVER A GIVEN TIME FRAME OPERATION 207, the patient's specific treatment experience with the prescribed/recommended medical treatment data obtained at OBTAIN THE PATIENT'S SPECIFIC TREATMENT EXPERIENCE DATA OPERATION 205 is correlated in time with the patient's prescribed/recommended medical treatment data, and the implementation/use of those treatments data, obtained and/or updated at OBTAIN THE PATIENT'S MEDICAL TREATMENT IMPLEMENTATION DATA OPERATION 203 to create processed data correlating the patient's specific treatment experience data with the patient's medical treatment implementation data.

In one embodiment, the patient's specific treatment experience data is correlated with the patient's medical treatment implementation data, or any other patient data desired, using mathematical and/or statistical analysis, such as regression analysis, and the correlation, along with an analysis of how strongly the data is correlated, is provided to the patient, and/or healthcare service providers, and/or any other designated parties.

In one embodiment, correlating the patient's specific treatment experience data with the patient's medical treatment implementation data at CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207 is performed under the control of a processor, such as CPU 101 of FIG. 1, a software process/application, or any combination thereof. Methods, means, procedures, processes, and/or mechanisms for correlating two sources of data in time are well known to those of skill in the art. In addition, the specific methods, means, procedures, processes, and/or mechanisms for correlating two sources of data in time will vary from computing system-to-computing system, from processor-to-processor, from application-to-application, from display format-to-display format, and from implementation-to-implementation. Consequently, a more detailed description of the methods, means, procedures, processes, and/or mechanisms for correlating two sources of data, such as the patient's specific treatment experience data and the patient's medical treatment implementation data, is omitted here to avoid detracting from the invention.

In one embodiment, once the patient's specific treatment experience with the prescribed/recommended medical treatment data obtained at OBTAIN THE PATIENT'S SPECIFIC TREATMENT EXPERIENCE DATA OPERATION 205 is correlated in time with the patient's prescribed/recommended medical treatment data, and the implementation/use of those treatments data, obtained and/or updated at OBTAIN THE PATIENT'S MEDICAL TREATMENT IMPLEMENTATION DATA OPERATION 203 at CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207 to create processed data correlating the patient's specific treatment experience data with the patient's medical treatment implementation data, process flow proceeds to PROVIDE THE PATIENT WITH THE CORRELATED PATIENT'S MEDICAL TREATMENT IMPLEMENTATION AND PATIENT'S SPECIFIC EXPERIENCE DATA OPERATION 209.

In one embodiment, at PROVIDE THE PATIENT WITH THE CORRELATED PATIENT'S MEDICAL TREATMENT IMPLEMENTATION AND PATIENT'S SPECIFIC EXPERIENCE DATA OPERATION 209, the processed data correlating the patient's specific treatment experience data with the patient's medical treatment implementation data of CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207 is provided to the patient in any one of various forms/formats.

As noted above, in one embodiment, the patient's specific treatment experience data is correlated with the patient's medical treatment implementation data, or any other patient data desired, using mathematical and/or statistical analysis, such as regression analysis, and the correlation, along with an analysis of how strongly the data is correlated, is provided to the patient, and/or healthcare service providers, and/or any other designated parties.

In one embodiment, at PROVIDE THE PATIENT WITH THE CORRELATED PATIENT'S MEDICAL TREATMENT IMPLEMENTATION AND PATIENT'S SPECIFIC EXPERIENCE DATA OPERATION 209 the processed data correlating the patient's specific treatment experience data with the patient's medical treatment implementation data is provided to the patient in the form of a visual display such as, but not limited to: a graphical display of results over time; a charting of results over time; a video representation; or any other primarily visual display. In other embodiments, the processed data correlating the patient's specific treatment experience data with the patient's medical treatment implementation data is provided to the patient in the form of an audio presentation, in a table of data, or in text format.

In one embodiment, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of any means for transferring, relaying and/or providing data in any form, to a user, such a patient, whether known at the time of filing or as developed thereafter.

For example, as noted above, in one embodiment, process for correlating medical treatments with symptoms and metrics 200 is part of a parent personal health management, personal financial, business financial, accounting, or tax preparation software system, program, package or application, such as computing system implemented process 180 of FIG. 1, that implements, includes, is accessed by, and/or is otherwise associated with process for correlating medical treatments with symptoms and metrics 200, as one of multiple features. In these embodiments, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 from, or through, the parent process.

In one embodiment, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of storing the data and then granting process for correlating medical treatments with symptoms and metrics 200 access to the data and/or providing the data on a computer program product.

In other embodiments, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of e-mail or through text messaging. In other embodiments, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

Figure 3:
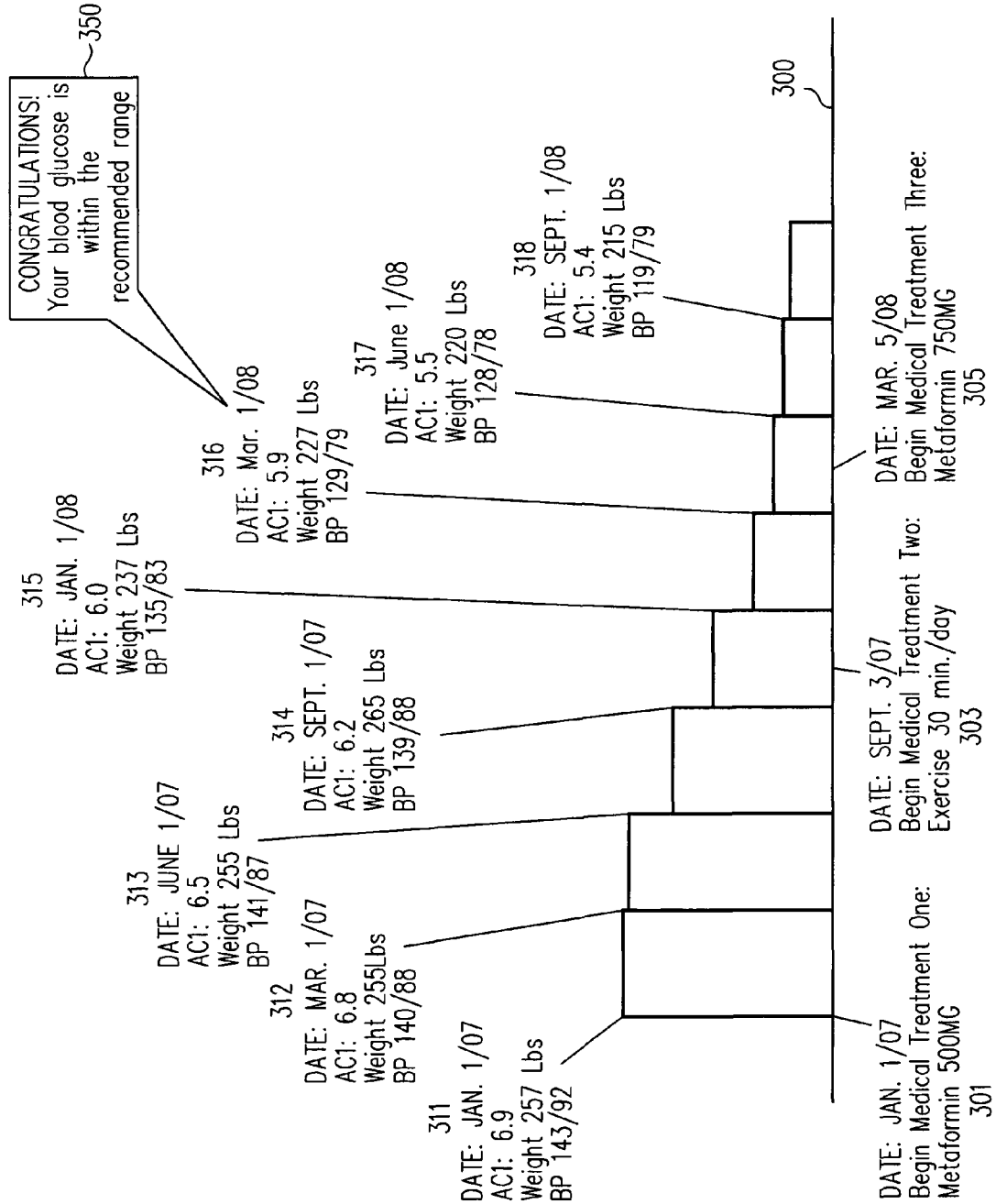
FIG. 3 is a exemplary representation of a visual display showing processed data correlating a patient's specific treatment experience data with treatment implementation data, in the form of a bar graph, in accordance with one embodiment.

As noted above, in one embodiment, the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 by way of a graphical display of results over time and/or a charting of results over time. FIG. 3 is an exemplary representation of a visual display showing processed data correlating a patient's specific treatment experience data with treatment implementation data over time, in the form of a bar graph, in accordance with one embodiment.

FIG. 3 shows one illustrative example of a bar graph display 300 as would be provided to a patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209 in accordance with one embodiment.

As seen in FIG. 3, bar graph 300 includes three medical treatment implementation data points 301, 303 and 305 for a given patient that include information obtained in an operation similar to OBTAIN THE PATIENT'S MEDICAL TREATMENT IMPLEMENTATION DATA OPERATION 203 of FIG. 2. In addition, returning to FIG. 3, bar graph 300 includes eight patient specific treatment experience data points 311, 312, 313, 314, 315, 316, 317, and 318 correlated on bar graph 300 as would be done in an operation similar to CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207 of FIG. 2.

In the particular illustrative example of FIG. 3, the correlated data (301, 303, 305 and 311-318) shown graphically on bar graph 300 relates to a patient that has been diagnosed with type-2 diabetes and has been prescribed three medical treatments over two years to control the patient's blood glucose levels. In this specific example, bar graph display 300 shows the patient's blood glucose readings as indicated by the common AC1 test. AC1 tests show an average blood glucose percentage over a three month period. Due to the averaged three month results, AC1 tests are often considered more reliable than "spot" tests. In general, it is highly desirable for a diabetic to maintain AC1 test results below 6.0, i.e., below 6.0%.

In the specific example of FIG. 3, it is stipulated the patient has been prescribed Metaformin to lower, and stabilize, the patient's blood glucose levels. In the example of FIG. 3, the patient is initially prescribed a "Medical Treatment One" consisting of 500 MG of Metaformin a day on Jan. 1, 2007 (see patient's medical treatment implementation data point 301 and patient specific treatment experience data point 311).

As can be seen in FIG. 3, in this specific example, patient's specific treatment experience data point 311 shows that on Jan. 1, 2007 the patient's AC1 test result was 6.9, weight was 257 pounds, and blood pressure was 143/92. As can also be seen in FIG. 3, in this specific example, patient's specific treatment experience data point 312 shows that on Mar. 1, 2007 the patient's AC1 test result was 6.8, weight was 255 pounds, and blood pressure was 140/88. As can also be seen in FIG. 3, in this specific example, patient's specific treatment experience data point 313 shows that on Jun. 1, 2007 the patient's AC1 test result was 6.5, weight was 255 pounds, and blood pressure was 141/87. As can also be seen in FIG. 3, in this specific example, patient's specific treatment experience data point 314 shows that on Sep. 1, 2007 the patient's AC1 test result was 6.2, weight was 256 pounds, and blood pressure was 139/88.

As can be seen in FIG. 3, and as discussed above, while on "Medical Treatment One" the patient enjoyed some success in that the patient's blood glucose levels dropped from 6.9% to 6.2%. In the specific example of FIG. 3, it is further stipulated that since the patient's results were not completely satisfactory as of patient's specific treatment experience data point 314, and Sep. 1, 2007, the patient was further requested to commence a "Medical Treatment Two" consisting of an exercise program of 20 minutes per day on Sep. 3, 2007 (see patient's medical treatment implementation data point 303).

As can be seen in FIG. 3, in this specific example, patient's specific treatment experience data point 315 shows that on Jan. 1, 2008 the patient's AC1 test result was 6.0, weight was 237 pounds, and blood pressure was 135/83. As can also be seen in FIG. 3, in this specific example, patient's specific treatment experience data point 316 shows that on Mar. 1, 2008 the patient's AC1 test result was 5.9, weight was 227 pounds, and blood pressure was 129/79.

As shown in FIG. 3, in one embodiment, process for correlating medical treatments with symptoms and metrics 200 (FIG. 2) can be used to provide a patient with encouragement and support as the patient passes established goals. In the example of FIG. 3, encouragement text 350 is shown. In one embodiment, encouragement text 350 informs the patient that a specific goal has been obtained. In this example, the patient's blood glucose levels have dropped below the 6.0% level to 5.9%. These encouragement messages can serve to inspire the patient to continue on with the medical treatment and to motivate the patient on to further gains. Those of skill in the art will recognize that text notations could also be used to point out negative changes and/or "back-sliding" as well.

As can be seen in FIG. 3, and as discussed above, while on "Medical Treatment One" and "Medical Treatment Two" the patient enjoyed significant success in that the patient's blood glucose levels dropped from 6.2% to 5.9%, the patient lost 29 pounds, and the patient's blood pressure dropped from 139/88 to 129/79.

In the specific example of FIG. 3, it is further stipulated that the patient was further requested to commence a "Medical Treatment Three" on Mar. 5, 2008 consisting of an increased dosage of Metaformin from 500 MG a day to 750 MG a day (see patient's medical treatment implementation data point 305).

As can be seen in FIG. 3, in this specific example, patient's specific treatment experience data point 317 shows that on Jun. 1, 2008 the patient's AC1 test result was 5.5, weight was 220 pounds, and blood pressure was 128/78. As can also be seen in FIG. 3, in this specific example, patient's specific treatment experience data point 318 shows that on Sep. 1, 2008 the patient's AC1 test result was 5.4, weight was 215 pounds, and blood pressure was 119/79.

Using a display such as bar graph 300 in FIG. 3, the patient is provided with a means for visually tracking his or her progress/results using the patient's specific treatment experience data correlated with the patient's medical treatment implementation data. Those of skill in the art will readily recognize that the specific data presented, the formatting of the data, the visual graphing of the data, and the display of text in FIG. 3 was shown for illustrative purposes only and that, in various embodiments, numerous other specific data can be presented, formatted, graphed, displayed, and described. Consequently, the specific example and illustration of FIG. 3 does not limit the invention as claimed below.

Returning to FIG. 2, in one embodiment, once the processed data correlating the patient's specific treatment experience data with the patient's medical treatment implementation data is provided to the patient at PROVIDE THE PATIENT WITH THE CORRELATED PATIENT'S MEDICAL TREATMENT IMPLEMENTATION AND PATIENT'S SPECIFIC EXPERIENCE DATA OPERATION 209, process flow proceeds to EXIT OPERATION 220 and process for correlating medical treatments with symptoms and metrics 200 is exited and/or returns to OBTAIN THE PATIENT'S MEDICAL TREATMENT IMPLEMENTATION DATA OPERATION 203 and/or OBTAIN THE PATIENT'S SPECIFIC TREATMENT EXPERIENCE DATA OPERATION 205 to await new data.

Using process for correlating medical treatments with symptoms and metrics 200, a patient is provided information showing his or her results and/or progress correlated with the implementation of a given medical treatment. Consequently, using process for correlating medical treatments with symptoms and metrics 200, the patient is provided feedback and comparative information showing the results and/or progress of his or her efforts. In many cases, this feedback provides the positive reinforcement necessary to keep the patient on the prescribed medical treatment. In addition, many patients may feel empowered and inspired by this information to take a more active role in maintaining their bodies and tracking their general state of health.

In one embodiment, baseline medical treatment data associated with a given medical treatment and/or procedure is also obtained. In one embodiment, the baseline medical treatment data includes the expected patient experience and/or results from the medical treatment and/or an expected time frame for those results, based on the typical patient experience and/or research data. In this embodiment, the patient's specific treatment experience data is compared with the baseline medical treatment data and then this information is provided to the patient. In this way, the patient can view their specific experience with, and/or results from, the medical treatment within the context of the expected and/or average progress/results of the medical treatment.

Figure 4:
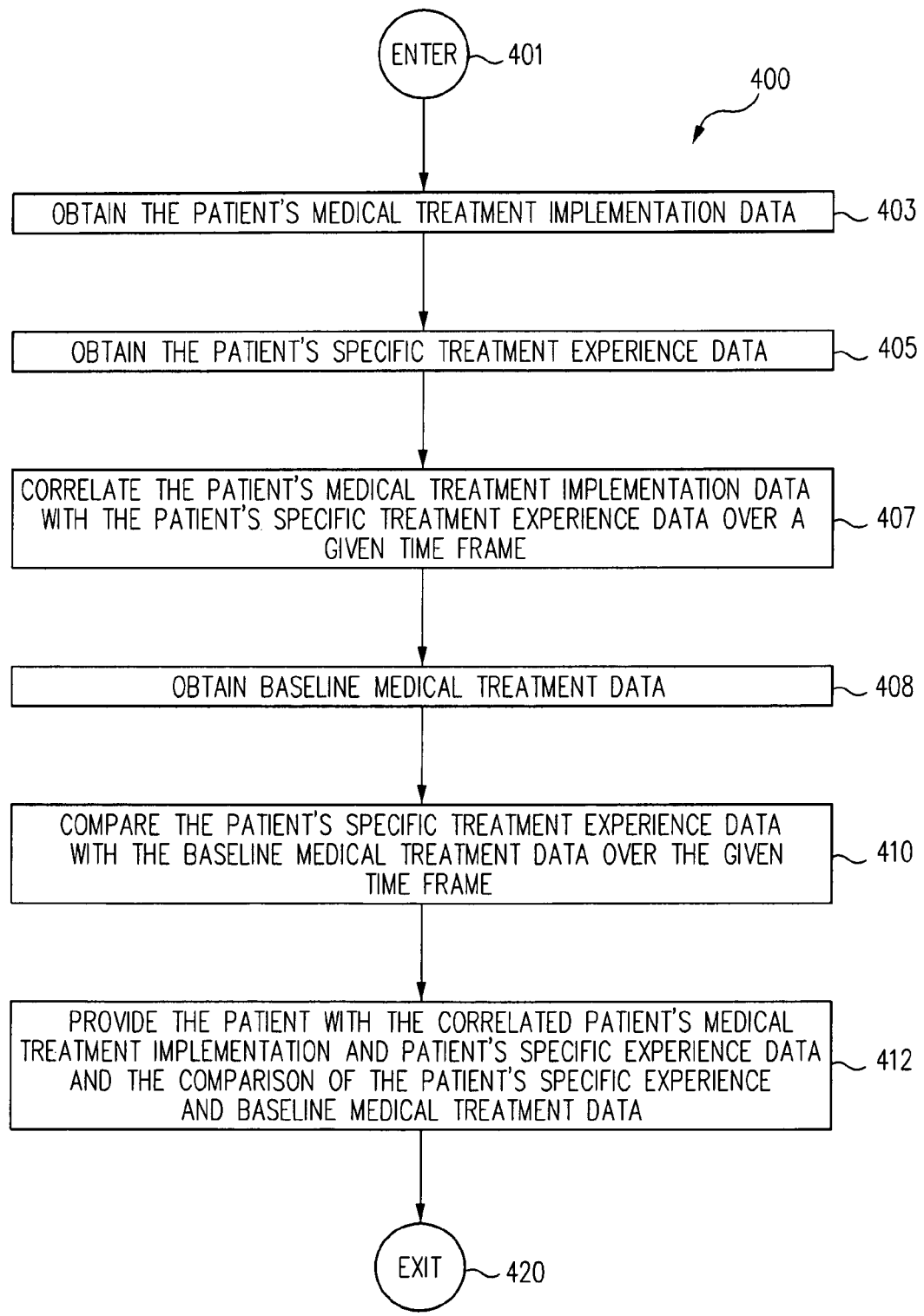
FIG. 4 is a flow chart depicting a process for correlating medical treatments with symptoms and metrics in accordance with one embodiment.

FIG. 4 is a flow chart depicting a process for correlating medical treatments with symptoms and metrics 400 in accordance with one embodiment. Process for correlating medical treatments with symptoms and metrics 400 begins at ENTER OPERATION 401 of FIG. 4 and process flow proceeds to OBTAIN THE PATIENT'S MEDICAL TREATMENT IMPLEMENTATION DATA OPERATION 403.

In one embodiment: OBTAIN THE PATIENT'S MEDICAL TREATMENT IMPLEMENTATION DATA OPERATION 403, OBTAIN THE PATIENT'S SPECIFIC TREATMENT EXPERIENCE DATA OPERATION 405, and CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407, of FIG. 4 and process for correlating medical treatments with symptoms and metrics 400, are substantially identical to: OBTAIN THE PATIENT'S MEDICAL TREATMENT IMPLEMENTATION DATA OPERATION 203, OBTAIN THE PATIENT'S SPECIFIC TREATMENT EXPERIENCE DATA OPERATION 205, and CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207, of FIG. 2 and process for correlating medical treatments with symptoms and metrics 200. Consequently, the discussion above with respect to: OBTAIN THE PATIENT'S MEDICAL TREATMENT IMPLEMENTATION DATA OPERATION 203, OBTAIN THE PATIENT'S SPECIFIC TREATMENT EXPERIENCE DATA OPERATION 205, and CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 207, is applicable to, and incorporated here for similarly labeled and numbered operations: OBTAIN THE PATIENT'S MEDICAL TREATMENT IMPLEMENTATION DATA OPERATION 403, OBTAIN THE PATIENT'S SPECIFIC TREATMENT EXPERIENCE DATA OPERATION 405, and CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407, of FIG. 4 and process for correlating medical treatments with symptoms and metrics 400.

In one embodiment, once the patient's specific treatment experience with the prescribed/recommended medical treatment data obtained at OBTAIN THE PATIENT'S SPECIFIC TREATMENT EXPERIENCE DATA OPERATION 405 is correlated in time with the patient's prescribed/recommended medical treatment data, and the implementation/use of those treatments data, obtained and/or updated at OBTAIN THE PATIENT'S MEDICAL TREATMENT IMPLEMENTATION DATA OPERATION 403 at CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407 to create processed data correlating the patient's specific treatment experience data with the patient's medical treatment implementation data, process flow proceeds to OBTAIN BASELINE MEDICAL TREATMENT DATA OPERATION 408.

In one embodiment, at OBTAIN BASELINE MEDICAL TREATMENT DATA OPERATION 408, background/baseline data regarding the specific medical treatment of OBTAIN THE PATIENT'S MEDICAL TREATMENT IMPLEMENTATION DATA OPERATION 403 is obtained.

In one embodiment, the baseline medical treatment data includes, but is not limited to: data regarding the expected results from the medical treatment and how those results are expected to manifest themselves, in terms of both time and the actual result; data regarding any side effects associated with the medical treatment, and how those symptoms are expected to manifest themselves in terms of both the symptom itself and time; and any other data regarding expected/average results associated with the prescribed medical treatment.

In one embodiment, the baseline medical treatment data is obtained from various sources, including, but not limited to: medication manufacturers and/or providers; clinical studies; government agencies; public and private watchdog groups; healthcare service providers; health insurance providers; health care product providers; the patient; and/or any other party or organization. In one embodiment, the baseline medical treatment data is obtained electronically and/or automatically for the patient by any one of various means known to those of skill in the art and/or as discussed herein. In one embodiment, the baseline medical treatment data is obtained through manual data entry using a user interface device.

As an example, in one embodiment, the baseline medical treatment data is obtained at OBTAIN THE BASELINE MEDICAL TREATMENT DATA OPERATION 408 from a database and/or web-page maintained by one or more of: medication manufacturers and/or providers; clinical studies; government agencies; public and private watchdog groups; healthcare service providers; health insurance providers; health care product providers; the patient; and/or any other party or organization.

In other embodiments, the data is obtained at OBTAIN THE BASELINE MEDICAL TREATMENT DATA OPERATION 408 by any means for obtaining, collecting, accessing, entering, transferring, relaying and/or providing data in any form, to a process, such as process for correlating medical treatments with symptoms and metrics 400, whether known at the time of filing or as developed thereafter.

For example, as noted above, in one embodiment, process for correlating medical treatments with symptoms and metrics 400 is part of a parent personal health management, personal financial, business financial, accounting, or tax preparation software system, program, package or application, such as computing system implemented process 180 of FIG. 1, that implements, includes, is accessed by, and/or is otherwise associated with process for correlating medical treatments with symptoms and metrics 400, typically as one of multiple features. In these embodiments, the data representing the baseline medical treatment may be obtained directly from, or through, the parent process.

In one embodiment, the baseline medical treatment data is obtained at OBTAIN THE BASELINE MEDICAL TREATMENT DATA OPERATION 408 from invoices/patient bills and/or claim data provided to process for correlating medical treatments with symptoms and metrics 400 by health care providers such as hospitals and/or doctors and/or other medical service personnel.

In some embodiments, the baseline medical treatment data is obtained at OBTAIN THE BASELINE MEDICAL TREATMENT DATA OPERATION 203 from any combination of the above sources and/or from any other source of data, whether known at the time of filing or as developed thereafter.

In one embodiment, the data representing the baseline medical treatment is stored, in whole, or in part, in a database maintained by, accessible by, owned by, or otherwise related to, a provider of process for correlating medical treatments with symptoms and metrics 400 by any one of the numerous mechanisms known to those of skill in the art. For instance, in one embodiment, the data, in whole, or in part, is stored in a memory system, such as memory system 103 or server memory system 123, or database 170, of FIG. 1, or in a cache memory, such as cache memory 103A of FIG. 1, or in any main memory or mass memory, associated with a computing device, such as computing system 100 described above. In one embodiment, the data, in whole, or in part, is stored in any computing device and/or server system, such as computing system 100 or server system 120, or other device, in another location, or on/in a computer readable medium, and/or any other computer program product, as defined herein. In one embodiment, the data, in whole, or in part, is stored on a webpage, in a web-based system or on a public network such as the Internet.

Returning to FIG. 4, in some embodiments, the data stored as described above is maintained, in whole, or in part, by: the provider of process for correlating medical treatments with symptoms and metrics 400; a computing system implemented process that is a parent process for process for correlating medical treatments with symptoms and metrics 400; the patient; a health insurance provider; a healthcare service provider; a third party data storage institution; a medication manufacturer and/or provider; clinical study groups; government agencies; public and private watchdog groups; and/or any other party or organization, and/or institution. In these embodiments, access to the data is then granted to process for correlating medical treatments with symptoms and metrics 400 at OBTAIN THE BASELINE MEDICAL TREATMENT DATA OPERATION 203 by providing access to the data and/or providing the data on a computer program product.

In other embodiments, the data representing the baseline medical treatment is provided through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, the data representing the baseline medical treatment is obtained/accessed/collected through e-mail or through text messaging. In other embodiments, the data representing the baseline medical treatment is provided to process for correlating medical treatments with symptoms and metrics 400 through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, the baseline medical treatment data is combined with/processed by analysis/input from experts in the medical field, scientists, clinical researchers, healthcare professionals, insurance experts, actuaries, and any other persons, groups, programs, applications, processes, means mechanisms and/or institutions capable of analyzing health data.

In one embodiment, once background/baseline data regarding the specific medical treatment of OBTAIN THE PATIENT'S MEDICAL TREATMENT IMPLEMENTATION DATA OPERATION 403 is obtained at OBTAIN BASELINE MEDICAL TREATMENT DATA OPERATION 408, process flow proceeds to COMPARE THE PATIENT'S SPECIFIC TREATMENT EXPERIENCE DATA WITH THE BASELINE MEDICAL TREATMENT DATA OVER THE GIVEN TIME FRAME OPERATION 410.

In one embodiment, at COMPARE THE PATIENT'S SPECIFIC TREATMENT EXPERIENCE DATA WITH THE BASELINE MEDICAL TREATMENT DATA OVER THE GIVEN TIME FRAME OPERATION 410 the patient's specific treatment experience with the prescribed/recommended medical treatment data obtained at OBTAIN THE PATIENT'S SPECIFIC TREATMENT EXPERIENCE DATA OPERATION 405 is compared with the baseline medical treatment data of OBTAIN BASELINE MEDICAL TREATMENT DATA OPERATION 408.

In one embodiment, comparing the patient's specific treatment experience data with the baseline medical treatment data is performed under the control of a processor, such as CPU 101 of FIG. 1, a software process/application, and/or any combination thereof. Methods, means, procedures, processes, and/or mechanisms for comparing data are well known to those of skill in the art. In addition, the specific methods, means, procedures, processes, and/or mechanisms for comparing the data will vary from computing system-to-computing system, from processor-to-processor, from application-to-application, from display format-to-display format, and from implementation-to-implementation. Consequently, a more detailed description of the methods, means, procedures, processes, and/or mechanisms for comparing data, such as the patient's specific treatment experience data and the baseline medical treatment data, is omitted here to avoid detracting from the invention.

In one embodiment, once the patient's specific treatment experience with the prescribed/recommended medical treatment data obtained at OBTAIN THE PATIENT'S SPECIFIC TREATMENT EXPERIENCE DATA OPERATION 405 is compared with the baseline medical treatment data of OBTAIN BASELINE MEDICAL TREATMENT DATA OPERATION 408 at COMPARE THE PATIENT'S SPECIFIC TREATMENT EXPERIENCE DATA WITH THE BASELINE MEDICAL TREATMENT DATA OVER THE GIVEN TIME FRAME OPERATION 410, process flow proceeds to PROVIDE THE PATIENT WITH THE CORRELATED PATIENT'S MEDICAL TREATMENT IMPLEMENTATION AND PATIENT'S SPECIFIC EXPERIENCE DATA AND THE COMPARISON OF THE PATIENT'S SPECIFIC EXPERIENCE AND BASELINE MEDICAL TREATMENT DATA OPERATION 412.

In one embodiment, at PROVIDE THE PATIENT WITH THE CORRELATED PATIENT'S MEDICAL TREATMENT IMPLEMENTATION AND PATIENT'S SPECIFIC EXPERIENCE DATA AND THE COMPARISON OF THE PATIENT'S SPECIFIC EXPERIENCE AND BASELINE MEDICAL TREATMENT DATA OPERATION 412, the processed/correlated data from CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407 and the comparison data of COMPARE THE PATIENT'S SPECIFIC TREATMENT EXPERIENCE DATA WITH THE BASELINE MEDICAL TREATMENT DATA OVER THE GIVEN TIME FRAME OPERATION 410 is provided to the patient.

In one embodiment, the processed/correlated data from CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407 and the comparison data of COMPARE THE PATIENT'S SPECIFIC TREATMENT EXPERIENCE DATA WITH THE BASELINE MEDICAL TREATMENT DATA OVER THE GIVEN TIME FRAME OPERATION 410 is provided to the patient in the form of a visual display such as, but not limited to: a graphical display of results over time; a charting of results over time; a video representation; or any other primarily visual display. In other embodiments, the data/information is provided to the patient in the form of an audio presentation, as a table of data, or in text format. In one embodiment, the data/information is provided to the patient in any format capable of conveying comparative/correlated data to a patient, whether known at the time of filing or as developed thereafter and/or as discussed herein.

Figure 5:
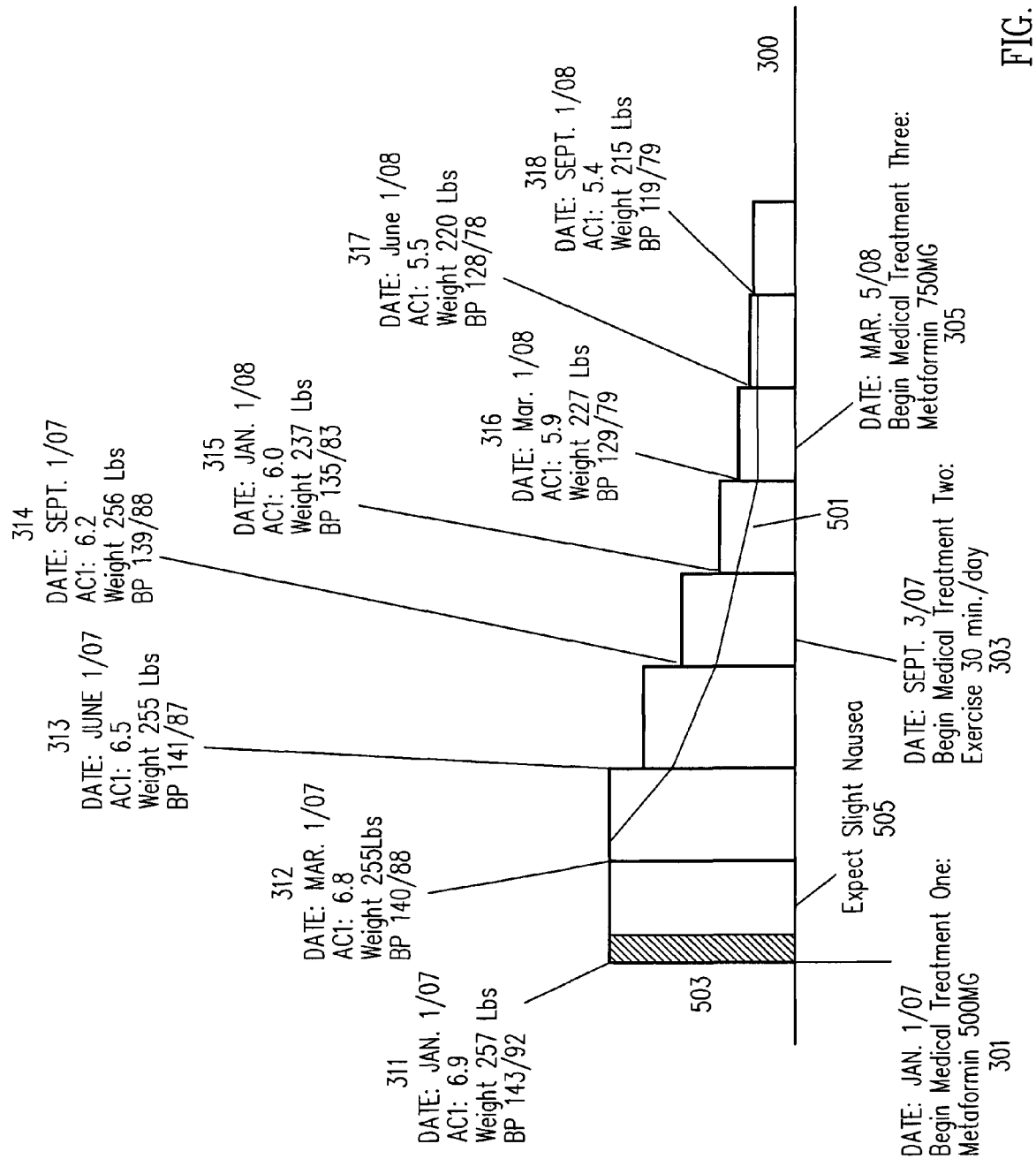
FIG. 5 is an exemplary representation of a visual display showing processed data correlating a patient's specific treatment experience data with treatment implementation data and baseline medical treatment data, in the form of a bar graph and line graph, in accordance with one embodiment.

FIG. 5 is an exemplary representation of a visual display showing processed data correlating patient's specific treatment experience data with treatment implementation data and baseline medical treatment data, in the form of a bar graph and line graph, in accordance with one embodiment. FIG. 5 includes the bar graph 300 of FIG. 3. However, in addition, FIG. 5 includes: baseline medical treatment data line 501; side-effect time window representation 403; and side-effect text 505.

As seen in FIG. 5, baseline medical treatment data line 501 shows the expected, or average, progression/results for the prescribed/recommended treatments. As seen in FIG. 5, baseline medical treatment data line 501 shows that, compared with the average data, the patient in this exemplary case responded somewhat slower than typical, but the end result was almost exactly as expected.

As also seen in FIG. 5, side-effect time window representation 503 and side-effect text 505 show that, in this specific illustrative example, the patient could have expected to have slight nausea during the first 3 weeks of treatment but that these symptoms should have ceased by the about the 3 week mark.

As noted above, FIG. 5, baseline medical treatment data line 501, side-effect time window representation 503, and side-effect text 505 help the patient visualize their experience in terms of the typical patient's experience. Thereby creating both an informed and, hopefully, motivated patient.

Those of skill in the art will readily recognize that the specific data presented, the formatting of the data, the visual graphing of the data, and the display of text in FIG. 5 was shown for illustrative purposes only and that, in various embodiments, numerous other specific data can be presented, formatted, graphed, displayed and described. Consequently, the specific example and illustration of FIG. 5 does not limit the invention as claimed below.

Returning to FIG. 4, in one embodiment, once the processed/correlated data from CORRELATE THE PATIENT'S MEDICAL TREATMENT IMPLEMENTATION DATA WITH THE PATIENT'S SPECIFIC TREATMENT EXPERIENCE DATA OVER A GIVEN TIME FRAME OPERATION 407 and the comparison data of COMPARE THE PATIENT'S SPECIFIC TREATMENT EXPERIENCE DATA WITH THE BASELINE MEDICAL TREATMENT DATA OVER THE GIVEN TIME FRAME OPERATION 410 is provided to the patient at PROVIDE THE PATIENT WITH THE CORRELATED PATIENT'S MEDICAL TREATMENT IMPLEMENTATION AND PATIENT'S SPECIFIC EXPERIENCE DATA AND THE COMPARISON OF THE PATIENT'S SPECIFIC EXPERIENCE AND BASELINE MEDICAL TREATMENT DATA OPERATION 412, process flow proceeds to EXIT OPERATION 420 and process for correlating medical treatments with symptoms and metrics 400 is exited and/or returns to OBTAIN THE PATIENT'S MEDICAL TREATMENT IMPLEMENTATION DATA OPERATION 403 and/or OBTAIN THE PATIENT'S SPECIFIC TREATMENT EXPERIENCE DATA OPERATION 405, and/or OBTAIN BASELINE MEDICAL TREATMENT DATA OPERATION 408 to await new data.

Using process for correlating medical treatments with symptoms and metrics 400, a patient is provided information showing his or her results and/or progress correlated with the implementation of a given medical treatment and information showing his or her results and/or progress as compared with expected results and/or progress for a given treatment. Consequently, using process for correlating medical treatments with symptoms and metrics 400, the patient is provided feedback and comparative information showing the results and/or progress of his or her efforts. As with process for correlating medical treatments with symptoms and metrics 200, in many cases, this feedback provided by process for correlating medical treatments with symptoms and metrics 400 further provides the positive reinforcement necessary to keep the patient on the prescribed medical treatment. In addition, using both process for correlating medical treatments with symptoms and metrics 200 and/or process for correlating medical treatments with symptoms and metrics 400, many patient's may feel empowered and inspired by this information and to take a more active role in maintaining their bodies and tracking their general state of health.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "defining", "accessing", "analyzing", "obtaining", "determining", "collecting", "identifying", "transferring", "storing", "notifying", "correlating", "comparing", "providing" etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter.

Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented process for correlating medical treatments with symptoms and metrics comprising:

using one or more processors associated with one or more computing systems to obtain historical medical treatment implementation data associated with a plurality of medical treatments previously recommended/prescribed to a patient, wherein the historical medical treatment implementation data comprises specific medication and/or medication regimens prescribed to the patient, whether the medications are utilized by the patient, when the medications are utilized by the patient, how the medications are utilized by the patient;

using one or more processors associated with one or more computing systems to obtain the patient's specific actual historical treatment experience data associated with the patient's specific actual historical experience with the previously recommended/prescribed medical treatments;

using one or more processors associated with one or more computing systems to obtain baseline medical treatment data associated with the medical treatments previously recommended/prescribed to a patient, the baseline medical treatment data including an expected patient experience and/or results from each one of the medical treatments and an expected time frame for those results, based on the typical patient experience;

using one or more processors associated with one or more computing systems to correlate the patient's specific actual historical treatment experience data, the baseline medical treatment data and the historical medical treatment implementation data to transform the patient's specific actual historical treatment experience data, the baseline medical treatment data and the patient's historical medical treatment implementation data into correlated specific actual historical treatment experience, baseline medical treatment data, and historical medical treatment implementation data;

using one or more processors associated with one or more computing systems to generate one or more visual displays based, at least in part, on the correlated specific actual historical treatment experience data, baseline medical treatment data, and historical medical treatment implementation data, the one or more visual displays including one or more historical medical treatment implementation data points correlated to one or more specific actual historical treatment experience data points with respect to time and further correlated to one or more baseline medical treatment data points; and providing the one or more visual displays to the patient.

2. The computing system implemented process for correlating medical treatments with symptoms and metrics of claim 1, wherein;

at least part of the historical medical treatment implementation data is obtained from a healthcare service provider as electronic data.

3. The computing system implemented process for correlating medical treatments with symptoms and metrics of claim 1, wherein;

at least part of the historical medical treatment implementation data is obtained from a health insurance provider.

4. The computing system implemented process for correlating medical treatments with symptoms and metrics of claim 1, wherein;

at least part of the historical medical treatment implementation data is obtained from Explanation of Benefits (EOB) data.

5. The computing system implemented process for correlating medical treatments with symptoms and metrics of claim 1, wherein;

at least part of the historical medical treatment implementation data is obtained through a computing system implemented process associated with the computing system implemented process for correlating medical treatments with symptoms and metrics.

6. The computing system implemented process for correlating medical treatments with symptoms and metrics of claim 1, wherein;

at least part of the patient's specific actual historical treatment experience data is obtained from a healthcare service provider as electronic data.

7. The computing system implemented process for correlating medical treatments with symptoms and metrics of claim 1, wherein;

at least part of the patient's specific actual historical treatment experience data is obtained through a computing system implemented process associated with the computing system implemented process for correlating medical treatments with symptoms and metrics.

8. The computing system implemented process for correlating medical treatments with symptoms and metrics of claim 1, wherein;

at least part of the baseline medical treatment data is obtained from a medication provider as electronic data.

9. The computing system implemented process for correlating medical treatments with symptoms and metrics of claim 1, wherein;

at least part of the baseline medical treatment data is obtained from a healthcare service provider as electronic data.

10. The computing system implemented process for correlating medical treatments with symptoms and metrics of claim 1, wherein;

at least part of the baseline medical treatment data is obtained through a computing system implemented process associated with the computing system implemented process for correlating medical treatments with symptoms and metrics.

11. A computer readable medium for correlating medical treatments with symptoms and metrics comprising:

a nontransitory computer readable medium having instructions stored thereon which when executed by one or more processors perform a process for correlating medical treatments with symptoms and metrics, the process comprising:

obtaining historical medical treatment implementation data associated with a plurality of medical treatments previously recommended/prescribed to a patient, wherein the historical medical treatment implementation data comprises specific medication and/or medication regimens prescribed to the patient, whether the medications are utilized by the patient, when the medications are utilized by the patient, how the medications are utilized by the patient;

using one or more processors associated with one or more computing systems to obtain the patient's specific actual historical treatment experience data associated with the patient's specific actual historical experience with the previously recommended/prescribed medical treatments;

using one or more processors associated with one or more computing systems to obtain baseline medical treatment data associated with a medical treatment previously recommended/prescribed to a patient, the baseline medical treatment data including an expected patient experience and/or results from the medical treatments and an expected time frame for those results, based on the typical patient experience;

using one or more processors associated with one or more computing systems to correlate the patient's specific actual historical treatment experience data, the baseline medical treatment data and the historical medical treatment implementation data to transform the patient's specific actual historical treatment experience data, the baseline medical treatment data and the patient's historical medical treatment implementation data into correlated specific actual historical treatment experience, baseline medical treatment data, and historical medical treatment implementation data;

using one or more processors associated with one or more computing systems to generate one or more visual displays based, at least in part, on the correlated specific actual historical treatment experience data, baseline medical treatment data, and historical medical treatment implementation data, the one or more visual displays including one or more historical medical treatment implementation data points correlated to one or more specific actual historical treatment experience data points with respect to time and further correlated to one or more baseline medical treatment data points; and providing the one or more visual displays to the patient.

12. The computer readable medium for correlating medical treatments with symptoms and metrics of claim 11, wherein;
    at least part of the historical medical treatment implementation data is obtained from a healthcare service provider as electronic data.

13. The computing system implemented process for correlating medical treatments with symptoms and metrics of claim 11, wherein;
    at least part of the historical medical treatment implementation data is obtained from a health insurance provider.

14. The computer readable medium for correlating medical treatments with symptoms and metrics of claim 11, wherein;
    at least part of the historical medical treatment implementation data is obtained from Explanation of Benefits (BOB) data.

15. The computer readable medium for correlating medical treatments with symptoms and metrics of claim 11, wherein;
    at least part of the historical medical treatment implementation data is obtained through a computing system implemented process associated with the computing system implemented process for correlating medical treatments with symptoms and metrics.

16. The computer readable medium for correlating medical treatments with symptoms and metrics of claim 11, wherein;
    at least part of the patient's specific actual historical treatment experience data is obtained from a healthcare service provider as electronic data.

17. The computer readable medium for correlating medical treatments with symptoms and metrics of claim 11, wherein;
    at least part of the patient's specific actual historical treatment experience data is obtained through a computing system implemented process associated with the computing system implemented process for correlating medical treatments with symptoms and metrics.

18. The computer readable medium for correlating medical treatments with symptoms and metrics of claim 11, wherein;
    at least part of the baseline medical treatment data is obtained from a medication provider as electronic data.

19. The computer readable medium for correlating medical treatments with symptoms and metrics of claim 11, wherein;
    at least part of the baseline medical treatment data is obtained from a healthcare service provider as electronic data.

20. The computer readable medium for correlating medical treatments with symptoms and metrics of claim 11, wherein;
    at least part of the baseline medical treatment data is obtained through a computing system implemented process associated with the computing system implemented process for correlating medical treatments with symptoms and metrics.

* * * * *

UNITED STATES PATENT AND TRADEMARK OFFICE
CERTIFICATE OF CORRECTION

| | | |
|---|---|---|
| PATENT NO. | : 7,930,191 B1 | Page 1 of 1 |
| APPLICATION NO. | : 12/021708 | |
| DATED | : April 19, 2011 | |
| INVENTOR(S) | : Lisa Herrup Rogers | |

It is certified that error appears in the above-identified patent and that said Letters Patent is hereby corrected as shown below:

In Column 32, line 7, Claim 14, replace "(BOB)" with --(EOB)--;

Signed and Sealed this
Second Day of October, 2012

David J. Kappos
*Director of the United States Patent and Trademark Office*